US010493021B2

(12) United States Patent
Pedroso De Oliveira et al.

(10) Patent No.: US 10,493,021 B2
(45) Date of Patent: Dec. 3, 2019

(54) COSMETIC ANTIOXIDANT FORMULATION FOR TOPICAL USE COMPRISING AN ASSOCIATION OF PLANT EXTRACTS, USE THEREOF

(71) Applicant: Natura Cosméticos S.A., Sáo Paulo (BR)

(72) Inventors: Ana Paula Pedroso De Oliveira, São Paulo (BR); Cristiane Calvo De Santi, São Paulo (BR); Gabriela Placoná Diniz, São Paulo (BR); Jenny Chu Yan Ling Okuda, São Paulo (BR); Juliana Carvalhães Lago, São Paulo (BR); Kelen Fabíola Arroteia, Sáo Paulo (BR)

(73) Assignee: NATURA COSMÉTICOS S.A., São Paulo (BR)

( * ) Notice: Subject to any disclaimer, the term of this patent is extended or adjusted under 35 U.S.C. 154(b) by 0 days.

(21) Appl. No.: 15/556,172

(22) PCT Filed: Mar. 4, 2016

(86) PCT No.: PCT/BR2016/050048
§ 371 (c)(1),
(2) Date: Sep. 6, 2017

(87) PCT Pub. No.: WO2016/141445
PCT Pub. Date: Sep. 15, 2016

(65) Prior Publication Data
US 2018/0161268 A1 Jun. 14, 2018

Related U.S. Application Data

(60) Provisional application No. 62/129,189, filed on Mar. 6, 2015.

(51) Int. Cl.
A61K 36/00 (2006.01)
A61K 8/9789 (2017.01)
A61Q 19/08 (2006.01)
A61K 8/97 (2017.01)
A61K 8/9728 (2017.01)
A61K 8/34 (2006.01)
A61K 8/368 (2006.01)
A61K 8/44 (2006.01)
A61K 8/49 (2006.01)
A61K 8/64 (2006.01)
A61K 8/73 (2006.01)

(52) U.S. Cl.
CPC .............. *A61K 8/9789* (2017.08); *A61K 8/34* (2013.01); *A61K 8/342* (2013.01); *A61K 8/345* (2013.01); *A61K 8/347* (2013.01); *A61K 8/368* (2013.01); *A61K 8/44* (2013.01); *A61K 8/498* (2013.01); *A61K 8/645* (2013.01); *A61K 8/73* (2013.01); *A61K 8/97* (2013.01); *A61K 8/9728* (2017.08); *A61Q 19/08* (2013.01); *A61K 2800/522* (2013.01)

(58) Field of Classification Search
CPC ..................................................... A61K 36/00
See application file for complete search history.

(56) References Cited

U.S. PATENT DOCUMENTS

| 8,318,797 | B2 | 11/2012 | Presty | |
|---|---|---|---|---|
| 2003/0105031 | A1* | 6/2003 | Rosenbloom | A61K 8/42 514/27 |
| 2004/0156873 | A1* | 8/2004 | Gupta | A61K 8/0212 424/401 |
| 2006/0251607 | A1* | 11/2006 | Golz-Berner | A61K 8/97 424/74 |
| 2010/0113588 | A1 | 5/2010 | Presty | |
| 2012/0171308 | A1 | 7/2012 | Da et al. | |
| 2012/0189565 | A1 | 7/2012 | Da Luz et al. | |
| 2014/0154191 | A1 | 6/2014 | Doucet et al. | |

FOREIGN PATENT DOCUMENTS

| KR | 2000058730 A | * 10/2000 |
|---|---|---|
| KR | 100848800 | 7/2008 |
| WO | WO-2011103449 | 8/2011 |
| WO | WO 2013/016257 A1 | 1/2013 |

OTHER PUBLICATIONS

Definition of grape seed extract from Wikipeida, accessed on Oct. 16, 2018, pp. 1-3 (Year: 2018).*
International Search Report dated Jul. 12, 2016 in International Application No. PCT/BR2016/050048.
Database GNPD [Online] MINTEL; Sep. 2010 (Sep. 2010), "Serum", XP002757766, Database accession No. 1409032.
Database GNPD [Online] MINTEL; Sep. 2011 (Sep. 2011), "Firming Body Cream", XP002757767, Database accession No. 1615488.
Database GNPD [Online] MINTEL; May 2014 (May 2014), "Body Wash", XP002757768, Database accession No. 2382777.
(Continued)

Primary Examiner — Qiuwen Mi
(74) Attorney, Agent, or Firm — Alston & Bird LLP

(57) ABSTRACT

The present invention provides stable antioxidant cosmetic formulations for topical use comprising green tea extract in combination with additional active compounds having the surprising ability to exert antioxidant effect on the skin, the use stable antioxidant cosmetic formulations, as well as a method for reducing and/or preventing oxidative stress in keratinous tissues.

5 Claims, 1 Drawing Sheet

(56) References Cited

OTHER PUBLICATIONS

Database GNPD[Online] MINTEL; Mar. 2010, "Luxury Squared Highlighter & Concealer", XP002757769, Database accession No. 1292878.
Database GNPD [Online] MINTEL; Apr. 2012 (Apr. 2012), "Toner", XP002757770, Database accession No. 1781278.
Database WPI Week 200918 Thomson Scientific, London, GB; AN 2009-B48145, XP002575553.
Database GNPD [Online] MINTEL; Oct. 2006 (Oct. 2006), "DNA Action Complex", XP002759740, Database accession No. 604445.
Database GNPD [Online] MINTEL; Feb. 2011 (Feb. 2011, "Serum", XP002759741, Database accession No. 1497915.
Database GNPD [Online] MINTEL; Nov. 2011 (Nov. 2011), "Antioxidant Perfect 10 Serum", XP002759742, Database accession No. 1676439.
Database GNPD [Online] MINTEL; Apr. 2012 (Apr. 2012, "The Oxygen Boost Daily Energizing Oxygen Elixir", XP002759743, Database accession No. 1764702.
Database GNPD [Online] MINTEL; Oct. 2014 (Oct. 2014), "Extreme Repair Cream", XP002759744, Database accession No. 2750269.
Written Opinion for Application No. PCT/BR2016/050048 dated Aug. 29, 2016, 12 pages.
Degăspari, C. H. et al., *Antioxidants Properties of Phenolic Compounds*, Visão Acadêmica, Curitiba, V. 5, N. 1 (2004) 33-40, 8 pages.
Rohr, M. et al., *Enzymes—Powerful Anti-Aging and Anti-Oxidant-Active, Ingredients Investigated by FOITS and Detection of ICL-S*, Proceedings XXIst IFSCC International Congress 2000, Berlin (2000) 278-286.
Shindo, Y. et al., *Recovery of Antioxidants and Reduction in Lipid Hydroperoxides in Murine Epidermis, and Dermis After Acute Ultraviolet Skin Exposure*, Photodermatol, Photoimmunol, Photomed. 10 (1994) 183-191.

\* cited by examiner

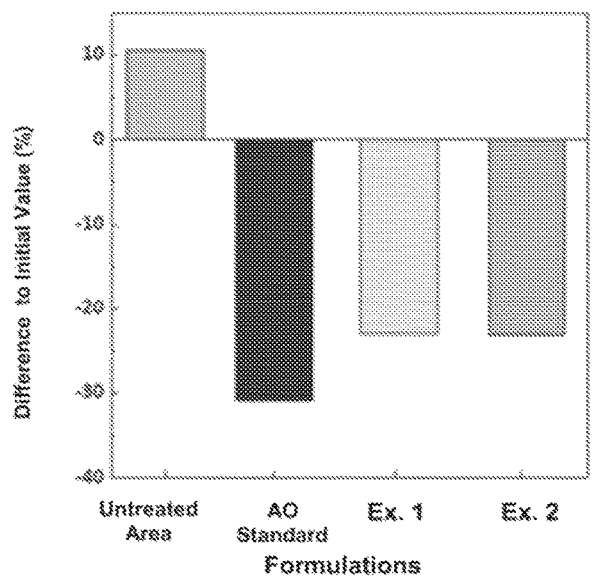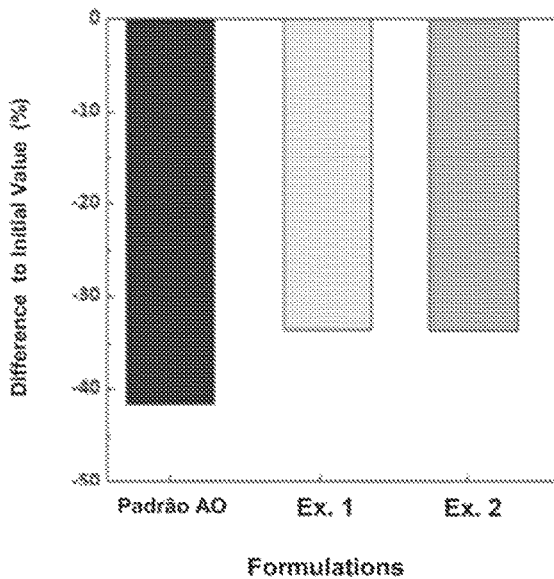

COSMETIC ANTIOXIDANT FORMULATION FOR TOPICAL USE COMPRISING AN ASSOCIATION OF PLANT EXTRACTS, USE THEREOF

GENERAL FIELD OF THE INVENTION

Free radicals are highly reactive molecules with unpaired electrons that can directly damage cell structures, membranes, lipids, proteins and DNA. The production of these reactive species can occur during normal metabolism or by various processes of oxidative stress induced by environmental factors such as pollution, ozone and sunlight. The production of free radicals tends to increase with age, whereas endogenous defence mechanisms tend to decrease. This leads to progressive damage to cell structures and results in aging.

In the electron transport chain, the formation of highly energetic intermediate species called reactive oxygen species (ROS), also classified as free radicals occurs. These molecules are capable of independent existence, and due to having one or more unpaired electrons have the ability to capture electrons of another molecule to stabilize, causing oxidation thereof.

Free radicals can initiate chain oxidation reactions that can damage cells or even cause their death. The consumption of oxygen by aerobic organisms and the generation of reactive oxygen species led to the "oxidative stress hypothesis". All cells, regardless of the organism used as the template manifest some level of oxidative stress.

During aging, the amount of oxidative damage increases exponentially. While damage to lipids and DNA are functional consequences of aging, oxidative damage in proteins may be the crucial factor in aging, leading to loss of catalytic activity and protein structural integrity.

The body itself has defence systems to neutralize or remove this damage, but the detection of such damage under normal physiological conditions, even in healthy bodies, suggests that the action of repair mechanisms and antioxidants do not reach 100% efficiency in the cell, resulting in an imbalance between the body's antioxidant defences and free radicals formed.

Antioxidants are substances that may protect against oxidative stress by neutralizing free radicals. Topical antioxidants are available in the market especially in products for skin care with the appeal of prevention of clinical signs of aging.

The use of antioxidants to neutralize free radicals in skin products is well disseminated. Moreover, antioxidants are essential components in cosmetic formulations to increase the shelf life of the product by reducing oxidative degradation of sensitive ingredients.

Plant extracts with antioxidant activity are already used in cosmetic compositions for treating keratinous tissues (WO2013016257 and U.S. Pat. No. 8,318,797). Plant extracts with antioxidant activity, are described, for example, by WO2013016257 and Degáspari et al., 2004. WO2010048686 teaches combinations comprising plant extracts with synergistic activity.

However, for the topical application of antioxidants are effective in preventing the aging, stability of the product is essential. As antioxidants are generally unstable, they can be oxidized and inactivated before reaching the target. The product should remain on the skin to reach the target tissue in the active form, and remain in place for some time to achieve the desired effects.

Therefore, there is a need in the art for stable cosmetic compositions comprising combinations of antioxidants are able to exert greater antioxidant effect.

BRIEF DESCRIPTION OF THE INVENTION

The present invention provides stable superior antioxidant cosmetic formulations for topical use able to reduce and/or prevent oxidative stress in keratinous tissue comprising plant extracts, the use of said formulations in the preparation of a cosmetic product, as well as a method for reducing and/or preventing oxidative stress in keratinous tissues.

DETAILED DESCRIPTION OF THE INVENTION

The present invention provides stable antioxidant cosmetic formulations for topical use comprising a combination of green tea extract (*Camellia sinensis*) and one or more additional active selected from the group consisting of aroeira (*Schinus terebinthifolius*) extract, grape oligomeric proanthocyanidins (OPC), cocoa extract, coffee extract, vitamin E, *Castanea sativa* seed extract (Recoverine®), hydrolyzed *Candida saitoana* extract (Celldetox®), soy protein (Glycine Soja) and a cosmetically acceptable carrier. The formulations of the present invention show surprising ability to reduce and/or prevent oxidative stress in keratinous tissues.

Preferably, the stable antioxidant cosmetic formulations of the present invention comprise from about 0.1% to about 15% of a combination of green tea extract and one or more additional active.

Preferably the formulations of the present invention comprise from about 001 to 0.5% green tea extract in combination with: about 0.01 to about 2.5% aroeira (*Schinus terebinthifolius*) extract, and/or about 0.01 to about 1% grape seed oligomeric proanthocyanidins (OPC), and/or about 0.01 to about 1% coffee extract, and/or about 0.01 to about 3% vitamin E and/or about 0.01 to about 1% cocoa extract, and/or about 0.2 to about 5% *Castanea sativa* seed extract (Recoverine®), and/or about 0.1 to about 3% hydrolyzed *Candida saitoana* extract (Celldetox®) and/or about 0.5 to about 15% soy protein.

The cosmetically acceptable carriers of the present invention include, but are not limited to, aqueous gels, alcoholic gels, ointments, oils, alcoholic or aqueous fluids, water in oil emulsions, oil in water emulsions, and water in silicone emulsions.

Preferably, the formulations of this invention comprise cosmetically acceptable accessory ingredients, optionally selected from the group comprising xanthan gum, glycerine, EDTA, sodium benzoate, phenoxyethanol, 2-hydroxy fatty alcohol alkoxylate, sodium polyacrylate, polysorbate 20, BHT, disaccharidic gums, ethylhexylglycerin, carbomer, butyleneglycol, acrylate polymers, PEG-40 hydrogenated castor oil, methylisothiazolinone, methylchloroisothiazolinone, propylene glycol, potassium sorbate, polyglyceryl caprylate, fragrance and water.

Preferably, the formulations of this invention comprise from 0 to about 5% of xanthan gum, about 0.1 to about 3% of glycerin, about 0.01 to about 0.1% of EDTA, about 0.1 to about 1.0% of sodium benzoate, about 0.1 to about 2% of phenoxyethanol, about 0.1 to about 3% of 2-hydroxy fatty alcohol alkoxylate, about 0 to about 2% of sodium polyacrylate, about 0 to about 4% of polysorbate 20, about 0.01 to about 0.1 of BHT, 0 to about 1% of fragrance and from about 80 to about 98% of water, preferably demineralized water.

The formulations of the present invention are prepared in a conventional manner known by the skilled technician.

The present invention further provides a method for reducing and/or preventing oxidative stress in keratinous tissues comprising applying the formulations provided by the present invention to said keratinous tissues, as well as the use of said formulation in the preparation of a cosmetic product for reducing and/or preventing oxidative stress in keratinous tissues.

BRIEF DESCRIPTION OF THE FIGURES

FIG. 1 (A-B): Percentage decay of ICL-S compared to the initial value (A) and corrected by the untreated area (B) obtained for the formulations of Examples 1 and 2.

EXAMPLES

Example 1

A formulation according to the present invention was produced by adding phases 1-8 shown in the table below in sequence. The ninth phase is prepared by mixing solubilizer, fragrance and BHT, stirring the mixture and then adding to the main mixture. The xanthan gum is slowly added until complete dispersion and the pH adjusted to between 5-6.

| Phase | Component | Concentration (%) | Amount (g) |
|---|---|---|---|
| 1 | Demineralised water | 94.1000 | 94.1000 |
| 10 | Xantham gum | 1.0000 | 1.0000 |
| 2 | Disodium EDTA | 0.0500 | 0.0500 |
| 3 | Sodium benzoate | 0.3000 | 0.3000 |
| 4 | Phenoxyethanol F | 0.8000 | 0.8000 |
| 5 | Aroeira extract | 0.2500 | 0.2500 |
| 6 | Grape seed OPC | 0.1000 | 0.1000 |
| 7 | Dry refined green tea extract | 0.1000 | 0.1000 |
| 8 | Glycerine | 1.5000 | 1.5000 |
| 9 | 2-hydroxy fatty alcohol alkoxylate | 1.5000 | 1.5000 |
| 9 | BHT | 0.0500 | 0.0500 |
| 9 | Fragrance | 0.2500 | 0.2500 |

Example 2

A formulation according to the present invention was produced by adding the phases 1-10, shown in the table below, according to the indicated sequence. Xanthan gum was then slowly added until complete dispersion. Phase 12 was prepared by mixing solubilizer, fragrance and BHT and added to the main mixture. The pH was adjusted to 5-6.

| Phase | Component | Concentration (%) | Amount (g) |
|---|---|---|---|
| 3 | Recoverine EL | 2.2000 | 2.2000 |
| 4 | Celldetox | 1.6500 | 1.6500 |
| 5 | Sodium Benzoate | 0.3000 | 0.3000 |
| 6 | Phenoxyethanol | 0.8000 | 0.8000 |
| 7 | Glycerine | 1.5000 | 1.5000 |
| 8 | Dry cacao extract | 0.0500 | 0.0500 |
| 9 | Soybean protein | 5.5000 | 5.5000 |
| 10 | Dry refined green tea extract | 0.1000 | 0.1000 |
| 1 | Demineralised water | 85.0500 | 85.0500 |
| 2 | Disodium EDTA | 1.0000 | 1.0000 |
| 11 | Xantham gum | 0.0500 | 0.0500 |
| 12 | BHT | 0.2500 | 0.2500 |
| 12 | Fragrance | 1.5000 | 15000 |
| 12 | 2-hydroxy fatty alcohol alkoxylate | 0.1500 | 0.1500 |

In Vivo Efficacy Tests: Antioxidant Potential

The in vivo efficacy test was performed to determine the antioxidant activity of the formulations of Examples 1 and 2 by a clinical study using the methodology of chemiluminescence.

UVA radiation is able to induce a cascade of pro-oxidative processes in human skin. This oxidative stress is primarily caused by free radicals and reactive oxygen species (ROS), which disrupt the balance between pro- and antioxidant reactions in living cells.

Part of the energy of these reactions is released as photons. This chemiluminescence is strongly related to the degree of damage to the skin, resulting from photo-aging to even more serious disorders such as skin cancer.

To prevent the accumulation of ROS in the skin, thus, preventing cell damage, all aerobic cells have an effective endogenous antioxidant system to reduce the negative effects of oxidative stress. Exposure to UVA radiation is able to weaken this endogenous protection system (SHINDO, Y.; WITT, E.; HAN, D.; TZENG, B.; NGUYEN, L.; PACKER, L. "Recovery of antioxidants and reduction in lipid hydroperoxides in murine epidermis. and dermis after acute ultraviolet skin exposure." Photodermatol. Photoimmunol. Photomed. 10, 183-191, 1994).

Due to its short lifetime and low concentration in human skin, the direct observation of free radicals and ROS is still a challenge. The induced chemiluminescence of human skin (ICL-S) is a convenient way to obtain information on the level of oxidative stress method in vivo. The reduction of ICL-S for active ingredients applied topically is a sensitive monitoring that provides biochemical and biophysical to a cellular level (ROHR, M.; BENARD, S.; SCHRADER, A "Enzymes powerful anti-aging and antioxidant-active, ingredients investigated by FOITS and detection of ICL-S. In cosmetic signs for the new century. Proceedings the 21st IFSCC Congress 2000" Verlag für chemische Industrie, Augsburg, Germany, 2000. 28).

The ICL-S signal is substantially detected by a photomultiplier tube (PMT), providing a continuous and non-invasive monitoring of oxidative stress in skin in vivo following the use of cosmetic products.

The technique of ICL-S works on the basis of single photon counting. This allows the in vivo data to have high stability and detectability.

Among photosensitive devices in use today, the PMT provides extremely high sensitivity and fast response. The ICL-S system has been specially developed to connect the detection of photons and induced UV radiation in the same device.

The volunteers underwent a two-week period of application of the test samples, and the sample was applied once daily at the same location in a quantity of 2 mg/cm$^2$. Two measures of S-ICL were performed: one before the first application and the other about 20 hours after the last application.

As a reference, an untreated area of skin and an area which received a standard antioxidant, were used as negative and positive control, respectively.

FIG. 1 (A) shows the values of the percentage difference of the measures of ICL-S, relative to initial value, (B) the values of the percentage difference of the measured and corrected by the untreated area.

The formulations of Examples 1 and 2 showed a significant decrease in signal ICL-S and significant difference from untreated area. Thus, formulations 1 and 2 show superior antioxidant activity.

The invention claimed is:

1. A stable antioxidant cosmetic formulation for topical use comprising a combination of:
   green tea extract;
   one or more additional active agents selected from the group consisting of aroeira extract, coffee extract, vitamin E, grape seed oligomeric proanthocyanidins (OPC), cocoa extract, *Castanea sativa* seed extract, hydrolyzed *Candida saitoana* extract, and soybean protein; and
   one or more cosmetically acceptable carriers or accessory ingredients,
   wherein the formulation comprises 0.1% to about 15% of a combination of the green tea extract and the one or more additional active agents, and
   wherein the formulation comprises about 0.1% of green tea extract, about 0.25% of aroeira extract, and about 0.1% of grape seed oligomeric proanthocyanidins (OPC).

2. The formulation of claim 1, wherein the cosmetically acceptable carriers are aqueous gels, alcoholic gels, ointments, oils, alcoholic or aqueous fluids, water in oil emulsions, oil in water emulsions, and water in silicone emulsions.

3. The formulation of claim 1, wherein the cosmetically acceptable accessory ingredients are selected from the group consisting of xanthan gum, glycerine, EDTA, sodium benzoate, phenoxyethanol, 2-hydroxy fatty alcohol alkoxylate, sodium polyacrylate, polysorbate 20, BHT, disaccharidic gums, ethylhexylglycerin, carbomer, butyleneglycol, acrylate polymers, PEG-40 hydrogenated castor oil, methylisothiazolinone, methylchloroisothiazolinone, propylene glycol, potassium sorbate, polyglyceryl caprylate, fragrance and water.

4. The composition of claim 1, comprising: about 0.01 to about 1% of coffee extract, and/or about 0.01 to about 3% of vitamin E, and/or about 0.01 to about 1% of cocoa extract, and/or about 0.2 to about 5% of *Castanea sativa* seed extract, and/or about 0.1 to about 3% of hydrolyzed *Candida saitoana* extract and/or about 0.5 to about 15% of soybean protein; and
   0 to about 5% of xanthan gum and/or about 0.1 to about 3% of glycerin, and/or about 0.01 to about 0.1% of EDTA, and/or about 0.1 to about 1.0% of sodium benzoate, and/or about 0.1 to about 2% of phenoxyethanol and/or about 0.1 to about 3% of 2-hydroxy fatty alcohol alkoxylate and/or about 0 to about 2% of sodium polyacrylate and/or about 0 to about 4% of polysorbate 20 and/or about 0.01 to about 0.1 of BHT, and/or 0 to about 1% of fragrance, and/or about 80 to about 98% of water.

5. The formulation of claim 1, comprising about 2.2% of *Castanea sativa* seed extract, about 1.65% of hydrolyzed *Candida saitoana* extract, about 0.05% of cocoa extract and about 5.5% soy protein.

* * * * *